(12) United States Patent  (10) Patent No.: US 8,116,910 B2
Walters et al.  (45) Date of Patent: Feb. 14, 2012

(54) TELEPRESENCE ROBOT WITH A PRINTER

(75) Inventors: Derek Walters, Goleta, CA (US);
Marco Pinter, Santa Barbara, CA (US);
Jonathan Southard, Santa Barbara, CA
(US); Charles S. Jordan, Santa Barbara,
CA (US)

(73) Assignee: Intouch Technologies, Inc., Goleta, CA (US)

( * ) Notice: Subject to any disclaimer, the term of this patent is extended or adjusted under 35 U.S.C. 154(b) by 1209 days.

(21) Appl. No.: 11/895,299

(22) Filed: Aug. 23, 2007

(65) Prior Publication Data

US 2009/0055023 A1 Feb. 26, 2009

(51) Int. Cl.
*G06F 19/00* (2011.01)
(52) U.S. Cl. .................................. 700/259; 434/262
(58) Field of Classification Search .................. 700/259,
700/245, 248, 260; 434/262, 267; 600/595;
318/628; 345/156, 184
See application file for complete search history.

(56) References Cited

U.S. PATENT DOCUMENTS

| | | |
|---|---|---|
| 3,821,995 A | 7/1974 | Aghnides |
| 4,413,693 A | 11/1983 | Derby |
| 4,471,354 A | 9/1984 | Smith |
| 4,519,466 A | 5/1985 | Shiraishi |
| 4,638,445 A | 1/1987 | Mattaboni |
| 4,709,265 A | 11/1987 | Silverman et al. |
| 4,733,737 A | 3/1988 | Falamak |
| 4,803,625 A | 2/1989 | Fu et al. |
| 4,875,172 A | 10/1989 | Kanayama |
| 4,977,971 A | 12/1990 | Crane, III et al. |
| 5,073,749 A | 12/1991 | Kanayama |
| 5,084,828 A | 1/1992 | Kaufman et al. |
| 5,130,794 A | 7/1992 | Ritchey |
| 5,186,270 A | 2/1993 | West |
| 5,305,427 A | 4/1994 | Nagata |
| 5,341,242 A | 8/1994 | Gilboa et al. |
| 5,341,854 A | 8/1994 | Zezulka et al. |
| 5,374,879 A | 12/1994 | Pin et al. |
| 5,419,008 A | 5/1995 | West |
| 5,441,047 A | 8/1995 | David et al. |
| 5,462,051 A | 10/1995 | Oka et al. |
| 5,486,853 A | 1/1996 | Baxter et al. |

(Continued)

FOREIGN PATENT DOCUMENTS

CA  2289697 A1  11/1998

(Continued)

OTHER PUBLICATIONS

F. Ando et al., "A Multimedia Self-service Terminal with Conferencing Functions", 1995, IEEE, pp. 357-362.

(Continued)

*Primary Examiner* — Dalena Tran
(74) *Attorney, Agent, or Firm* — Paul Evans

(57) ABSTRACT

A remote controlled robot system that includes a robot and a remote controlled station. The robot includes a camera and a printer coupled to a mobile platform. The remote control station may display one or more graphical user interfaces with data fields. The graphical user interfaces allow a user to enter information into the data fields. The information is then transmitted to the robot and printed by the robot printer. The information may include a medical prescription and the name of the patient. Providing a robot printer allows the user to directly provide a medical prescription while remotely observing and interacting with the patient.

12 Claims, 9 Drawing Sheets

U.S. PATENT DOCUMENTS

| | | | |
|---|---|---|---|
| 5,510,832 A | 4/1996 | Garcia | |
| 5,544,649 A | 8/1996 | David et al. | |
| 5,553,609 A | 9/1996 | Chen et al. | |
| 5,572,229 A | 11/1996 | Fisher | |
| 5,630,566 A | 5/1997 | Case | |
| 5,636,218 A | 6/1997 | Ishikawa et al. | |
| 5,701,904 A | 12/1997 | Simmons et al. | |
| 5,762,458 A | 6/1998 | Wang et al. | |
| 5,786,846 A | 7/1998 | Hiroaki | |
| 5,802,494 A | 9/1998 | Kuno | |
| 5,836,872 A | 11/1998 | Kenet et al. | |
| 5,838,575 A | 11/1998 | Lion | |
| 5,857,534 A | 1/1999 | DeValult et al. | |
| 5,871,451 A | 2/1999 | Unger et al. | |
| 5,917,958 A | 6/1999 | Nunally et al. | |
| 5,959,423 A | 9/1999 | Nakanishi et al. | |
| 5,966,130 A | 10/1999 | Benman, Jr. | |
| 6,006,946 A | 12/1999 | Williams et al. | |
| 6,036,812 A | 3/2000 | Williams et al. | |
| 6,133,944 A | 10/2000 | Braun et al. | |
| 6,135,228 A | 10/2000 | Asada et al. | |
| 6,170,929 B1 | 1/2001 | Wilson et al. | |
| 6,211,903 B1 | 4/2001 | Bullister | |
| 6,219,587 B1 | 4/2001 | Ahlin et al. | |
| 6,232,735 B1 | 5/2001 | Baba et al. | |
| 6,233,504 B1 | 5/2001 | Das et al. | |
| 6,233,735 B1 | 5/2001 | Ebihara | |
| 6,256,556 B1 | 7/2001 | Zenke | |
| 6,259,806 B1 | 7/2001 | Green | |
| 6,292,713 B1 | 9/2001 | Jouppi et al. | |
| 6,304,050 B1 | 10/2001 | Skaar et al. | |
| 6,325,756 B1 | 12/2001 | Webb et al. | |
| 6,330,493 B1 | 12/2001 | Takahashi et al. | |
| 6,346,950 B1 | 2/2002 | Jouppi | |
| 6,369,847 B1 | 4/2002 | James et al. | |
| 6,430,471 B1 | 8/2002 | Kintou et al. | |
| 6,430,475 B2 | 8/2002 | Okamoto et al. | |
| 6,438,457 B1 | 8/2002 | Yokoo et al. | |
| 6,463,361 B1 | 10/2002 | Wang et al. | |
| 6,466,844 B1 | 10/2002 | Ikeda et al. | |
| 6,474,434 B1 | 11/2002 | Bech | |
| 6,491,701 B2 | 12/2002 | Tierney et al. | |
| 6,496,099 B2 | 12/2002 | Wang et al. | |
| 6,507,773 B2 | 1/2003 | Parker et al. | |
| 6,522,906 B1 | 2/2003 | Salisbury et al. | |
| 6,532,404 B2 | 3/2003 | Colens | |
| 6,535,182 B2 | 3/2003 | Stanton | |
| 6,535,793 B2 * | 3/2003 | Allard | 700/259 |
| 6,543,899 B2 | 4/2003 | Covannon et al. | |
| 6,549,215 B2 * | 4/2003 | Jouppi | 345/660 |
| 6,581,798 B2 * | 6/2003 | Liff et al. | 221/13 |
| 6,587,750 B2 | 7/2003 | Gerbi et al. | |
| 6,594,552 B1 | 7/2003 | Nowlin et al. | |
| 6,646,677 B2 | 11/2003 | Noro et al. | |
| 6,666,374 B1 | 12/2003 | Green et al. | |
| 6,684,129 B2 | 1/2004 | Salisbury et al. | |
| 6,691,000 B2 | 2/2004 | Nagai et al. | |
| 6,799,065 B1 | 9/2004 | Niemeyer | |
| 6,799,088 B2 | 9/2004 | Wang et al. | |
| 6,804,656 B1 | 10/2004 | Rosenfeld et al. | |
| 6,836,703 B2 | 12/2004 | Wang et al. | |
| 6,839,612 B2 | 1/2005 | Sanchez et al. | |
| 6,840,904 B2 | 1/2005 | Goldberg | |
| 6,845,297 B2 | 1/2005 | Allard | |
| 6,852,107 B2 | 2/2005 | Wang et al. | |
| 6,871,117 B2 | 3/2005 | Wang et al. | |
| 6,879,879 B2 | 4/2005 | Jouppi et al. | |
| 6,892,112 B2 | 5/2005 | Wang et al. | |
| 6,914,622 B1 | 7/2005 | Smith et al. | |
| 6,925,357 B2 | 8/2005 | Wang et al. | |
| 6,954,635 B2 * | 10/2005 | Kim et al. | 455/418 |
| 6,995,664 B1 | 2/2006 | Darling | |
| 7,115,102 B2 | 10/2006 | Abbruscato | |
| 7,123,285 B2 | 10/2006 | Smith et al. | |
| 7,154,526 B2 | 12/2006 | Foote et al. | |
| 7,156,809 B2 | 1/2007 | Quy | |
| 7,161,322 B2 | 1/2007 | Wang et al. | |
| 7,164,969 B2 | 1/2007 | Wang et al. | |
| 7,174,238 B1 | 2/2007 | Zweig | |
| 7,188,000 B2 | 3/2007 | Chiappetta et al. | |
| 2001/0037163 A1 | 11/2001 | Allard | |
| 2001/0054071 A1 | 12/2001 | Loeb | |
| 2002/0027597 A1 | 3/2002 | Sachau | |
| 2002/0057279 A1 | 5/2002 | Jouppi | |
| 2002/0058929 A1 | 5/2002 | Green | |
| 2002/0063726 A1 | 5/2002 | Jouppi | |
| 2002/0120362 A1 | 8/2002 | Lathan et al. | |
| 2002/0130950 A1 | 9/2002 | James et al. | |
| 2002/0141595 A1 | 10/2002 | Jouppi | |
| 2002/0183894 A1 | 12/2002 | Wang et al. | |
| 2003/0048481 A1 | 3/2003 | Kobayashi | |
| 2003/0050733 A1 | 3/2003 | Wang et al. | |
| 2003/0060808 A1 | 3/2003 | Wilk | |
| 2003/0100892 A1 | 5/2003 | Morley et al. | |
| 2003/0114962 A1 | 6/2003 | Niemeyer | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0220541 A1 | 11/2003 | Salisbury et al. | |
| 2004/0019406 A1 | 1/2004 | Wang et al. | |
| 2004/0088077 A1 | 5/2004 | Jouppi et al. | |
| 2004/0117065 A1 | 6/2004 | Wang et al. | |
| 2004/0143421 A1 | 7/2004 | Wang et al. | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0174129 A1 | 9/2004 | Wang et al. | |
| 2004/0215490 A1 | 10/2004 | Duchon et al. | |
| 2005/0021182 A1 | 1/2005 | Wang et al. | |
| 2005/0021183 A1 | 1/2005 | Wang et al. | |
| 2005/0021187 A1 | 1/2005 | Wang et al. | |
| 2005/0024485 A1 | 2/2005 | Castles et al. | |
| 2005/0027794 A1 | 2/2005 | Decker | |
| 2005/0028221 A1 | 2/2005 | Liu et al. | |
| 2005/0035862 A1 | 2/2005 | Wildman et al. | |
| 2005/0038416 A1 | 2/2005 | Wang et al. | |
| 2005/0052527 A1 | 3/2005 | Remy et al. | |
| 2005/0065438 A1 | 3/2005 | Miller | |
| 2005/0065659 A1 | 3/2005 | Tanaka et al. | |
| 2005/0110867 A1 | 5/2005 | Schultz | |
| 2005/0204438 A1 | 9/2005 | Wang et al. | |
| 2006/0047365 A1 | 3/2006 | Ghodoussi et al. | |
| 2006/0064212 A1 | 3/2006 | Thorne | |
| 2006/0259193 A1 | 11/2006 | Wang et al. | |
| 2007/0064092 A1 | 3/2007 | Sandbeg et al. | |
| 2007/0120965 A1 | 5/2007 | Sandberg et al. | |

FOREIGN PATENT DOCUMENTS

| | | |
|---|---|---|
| EP | 0981905 B1 | 1/2002 |
| JP | 07-257422 A | 10/1995 |
| JP | 08-084328 A | 3/1996 |
| JP | 2000-032319 A | 1/2000 |
| JP | 2002-046088 A | 2/2002 |
| JP | 2002-305743 A | 10/2002 |

OTHER PUBLICATIONS

Baltus et al., "Towards Personal Service Robots for the Elderly", Computer Science and Robotoics.

Bar-Cohen et al., Virtual reality robotic telesurgery simulations using MEMICA haptic system, Mar. 5, 2001, Internet, pp. 1-7.

Bauer, Jeffrey C., "Service Robots in Health Care: The Evolution of Mechanical Solutions to Human Resource Problems", Jun. 2003.

Bauer, John et al., "Remote telesurgical mentoring: feasibility and efficacy", 2000, IEEE, pp. 1-9.

Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.

Brooks, Rodney, Abstracts from Flesh & Machines, How Robots Will Change Us, "Remote Presence", p. 131-147, Feb. 2002.

Celi et al., "The eICU: It's not just telemedicine", Critical Care Medicine, vol. 29, No. 8 (Supplement), Aug. 2001.

Cleary et al., "State of the art in surgical robotics: Clinical applications and technology challenges", Feb. 24, 2002 Internet, pp. 1-26.

CNN, Floating 'droids' to roam space corridors of the future, Jan. 12, 2000, Internet, pp. 1-4.
CNN.com/Technology, Paging R.Robot: Machine helps doctors with patients, Sep. 30, 2003, Internet, 1-3.
Davies, "Robotics in Minimally Invasive Surgery", 1995, Internet, pp. 5/1-5/2.
DiGiorgio, James, "Is Your Emergency Department of the 'Leading Edge'?", 2005, Internet, pp. 1-4.
Elhajj et al., "Supermedia in Internet-based telerobotic operations", 2001, Internet, pp. 1-14.
Ellison et al., "Telerounding and Patient Satisfaction Following Surgery".
Goldberg et al., "Collaborative Teleoperation via the Internet", IEEE International Conference on Robotics and Automation, Apr. 2000, San Francisco, California.
Goldman, Lea, "Machine Dreams", Entrepreneurs, Forbes, May 27, 2002.
Gump, Michael D., "Robot Technology Improves VA Pharmacies", 2001, Internet, pp. 1-3.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
F.A. Candelas Herias et al., "Flexible virtual and remote laboratory for teaching Robotics", FORMATEX 2006, Proc. Advance in Control Education, Madrid, Spain, Jun. 21-23, 2006.
Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.
Ivanova, Natali, "Master's thesis: Internet Based Interface for Control of a Mobile Robot", Department of Numerical Analysis and Computer Science.
Johanson, Supporting video-mediated communication over the Internet, Chalmers Universiry of Technology, Dept of Computer Engineering, Gothenburg, Sweden, 2003.
Jouppi, et al., :Mutually-Immersive Audio Telepresence, Audio Engineering Society Convention Paper, presented at 113$^{th}$ Convention Oct. 2002.
Jouppi, Norman P., "First Steps Towards Mutually-Immersive Mobile Telepresence", CSCW '02, Nov. 16-20, 2002, New Orleans LA.
Kanehiro, Fumio et al., Virtual Humanoid Robot Platform to Develop Controllers of Real Humanoid Robots without Porting, 2001, IEEE, pp. 3217-3276.
Kaplan et al., "An Internet Accessible Telepresence".
Kuzuoka et al., "Can the GestureCam Be a Surrogate?".
Lim, Hun-ok et al., Control to Realize Human-like Walking of a Biped Humanoid Robot, IEEE 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs (2004).
Loeb, Gerald, "Virtual Visit: Improving Communication for Those Who Need It Most", 2001.
Mack, "Minimally invasive and robotic surgery", 2001, Internet IEEE, pp. 568-572.
Magne Charge—Smart Power for Electric Vehicles, Internet, Jun. 27, 2002.
Martin, Anya, "Days Ahead", Assisted Living Today, vol. 9, Nov./Dec. 2002, pp. 19-22.
McCardle et al., "The challenge of utilizing new technology in design education", 2000 Internet, pp. 122-127.

"More Online Robots, Robots that Manipulate", Internet, http://ford.ieor.berkeley.edu/ir/robots_a2.html, Feb. 2007.
Nakajima et al., "A Multimedia Teleteaching System sing an Electronic Whiteboard for Two-Way Communication of Motion Videos and Chalkboards", 1993, IEEE, pp. 436-441.
Ogata et al., "Development of Emotional Communication Robot: WAMOEBA-2r—Esperimental evaluation . . . ", 2000 IEEE, pp. 175-180.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, Eric John, "Personal Tele-Embodiment", Fall 2001.
Paulos, et al. , "Ubiquitous Tele-embodiment: Applications and Implications", International Journal of Human Computer Studies, Jun. 1997, vol. 46, No. 6, pp. 861-877.
Paulos, et al., "Designing Personal Tele-Embodiment", Presented at the IEEE International Conference on Robotics and Animation, Leuven, Belgium, May 20, 1998.
Pin et al., "A New Family of Omnidirectional and Holonomic Wheeled Platforms for Mobile Robots", IEEE, vol. 10, No. 4, Aug. 1994.
Roland Piquepaille's Technology Trends, "How new technologies are modifying your way of life", 2003, Internet, pp. 1-2.
PYXIS HELPMATE®, the Trackless Robotic Courier, Internet, 3 pgs.
Robot Hardware Mobile Robotics Research Group, Edinburgh, "Mobile Robotics Research Group", 2000 Internet, pp. 1-2.
Roy et al., "Towards Personal Service Robots for the Elderly", Internet, Mar. 7, 2002.
Salemi et al, "MILO: Personal robot platform", 2005, Internet, pp. 1-6.
Sandt, Frederic et al., "Perceptions for a Transport Robot in Public Environments", 1997, IROS '97.
Shimoga et al., Touch and force reflection for telepresence surgery, 1994, IEEE, pp. 1049-1050.
Stephenson, Gary, "Dr. Robot Tested at Hopkins", Aug. 5, 2003, Internet, pp. 1-2.
Stoianovici et al., "Robotic Tools for Minimally Invasive Urologic Surgery", Dec. 2002, Internet, 1-17.
Tendick et al., "Human-Machine Interfaces for Minimally Invasive Surgery", 1997, IEEE, pp. 2771-2776.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Urquhart, Kim, "InTouch's robotic Companion 'beams up' healthcare experts", Medical Device Daily, vol. 7, No. 39, Feb. 27, 2003, p. 1, 4.
Weiss et al., Telework and video-mediated communication: Importance of real-time, interactive communication for workers with disabilities, 1999, Internet, pp. 1-4.
Yamasaki et al., Applying Personal Robots and Active Interface to Video Conference Systems, 1995, Internet, pp. 243-248.
Yong et al., "Robot task execution with telepresence using virtual reality technology", 1998, Internet, pp. 1-9.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision/vision.html, Mar. 5, 1996.

* cited by examiner

TELEPRESENCE ROBOT WITH A PRINTER

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The Treviranus patent also discloses embodiments with a mobile platform, and different mechanisms to move the camera and the monitor.

There has been marketed a mobile robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

The InTouch robot system can be used by doctors to remotely view and diagnose patients. For example, a doctor can move the robot from room to room at a medical facility to observe and interact with patients. If the diagnosis requires the prescription of drugs the doctor must fax the prescription to the medical facility. This process can be time consuming and is ripe for error. It would be desirable to provide a remote control robot system that would allow the user to more readily provide a patient with a prescription or other information.

BRIEF SUMMARY OF THE INVENTION

A remote controlled robot that has a camera and an output device such as a printer coupled to a mobile platform.

DETAILED DESCRIPTION

Disclosed is a remote controlled robot system that includes a robot and a remote controlled station. The robot includes a camera and a printer coupled to a mobile platform. The remote control station may display one or more graphical user interfaces with data fields. The graphical user interfaces allow a user to enter information into the data fields. The information is then transmitted to the robot and printed by the robot printer. The information may include a medical prescription and the name of the patient. Providing a robot printer allows the user to directly provide a medical prescription while remotely observing and interacting with a patient.

Figure 1:
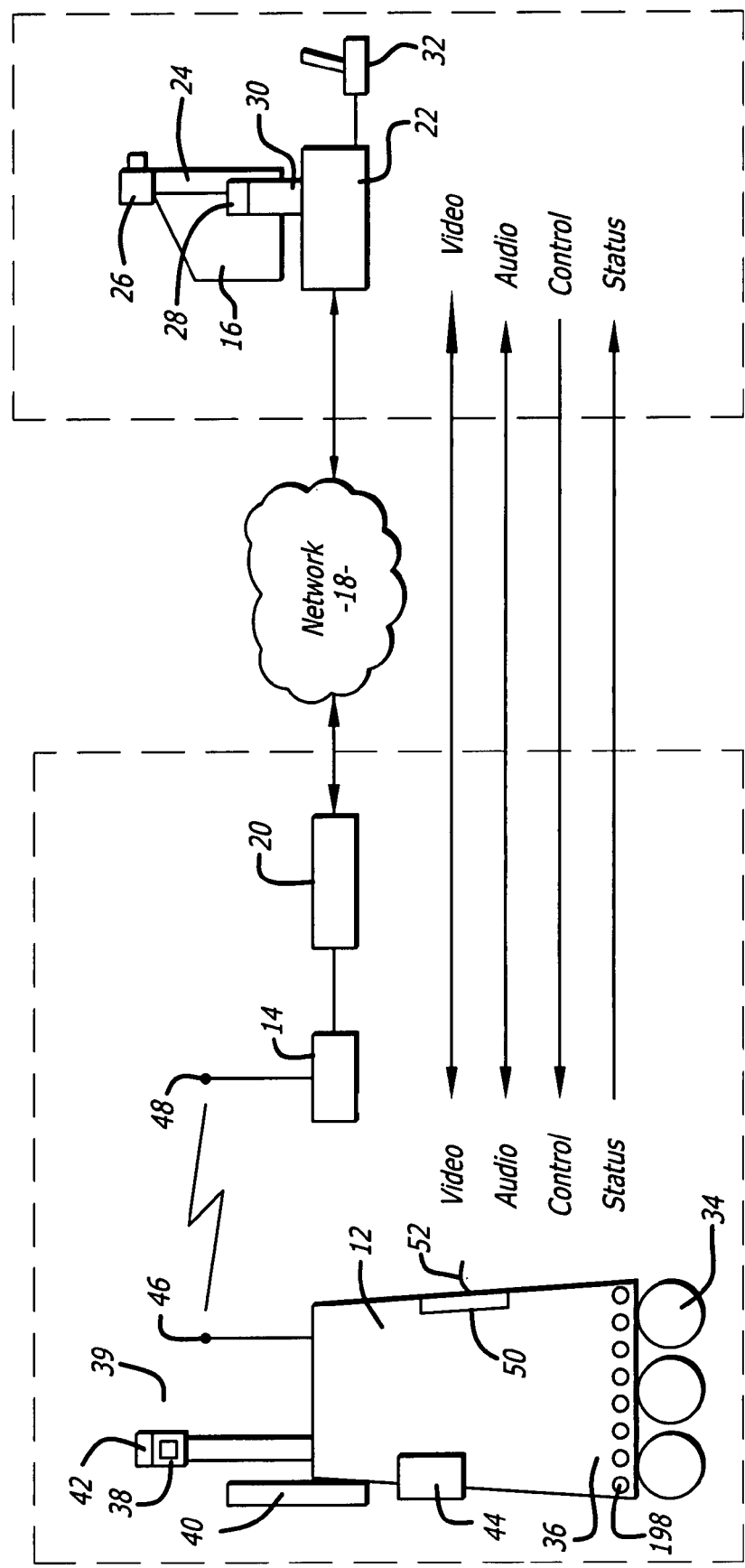
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 is a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a subject such as a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The robot 12 includes a printer 50 that is attached to the robot housing 36 and coupled to the mobile platform 34. The printer 50 can print information on printer paper 52 attached thereto. To minimize space and the profile of the robot the printer 50 may be a customized panel mounted thermal device. The printer 50 can print information provided by the remote control station 16.

Figure 2:
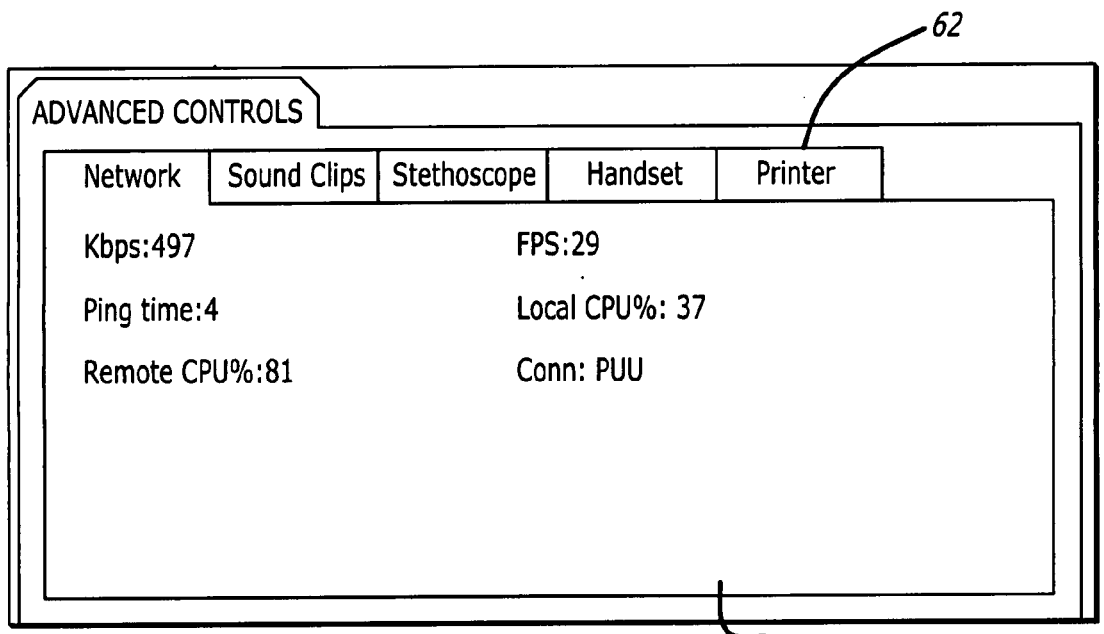
FIG. 2 is an illustration of a graphical user interface.
Figure 3:
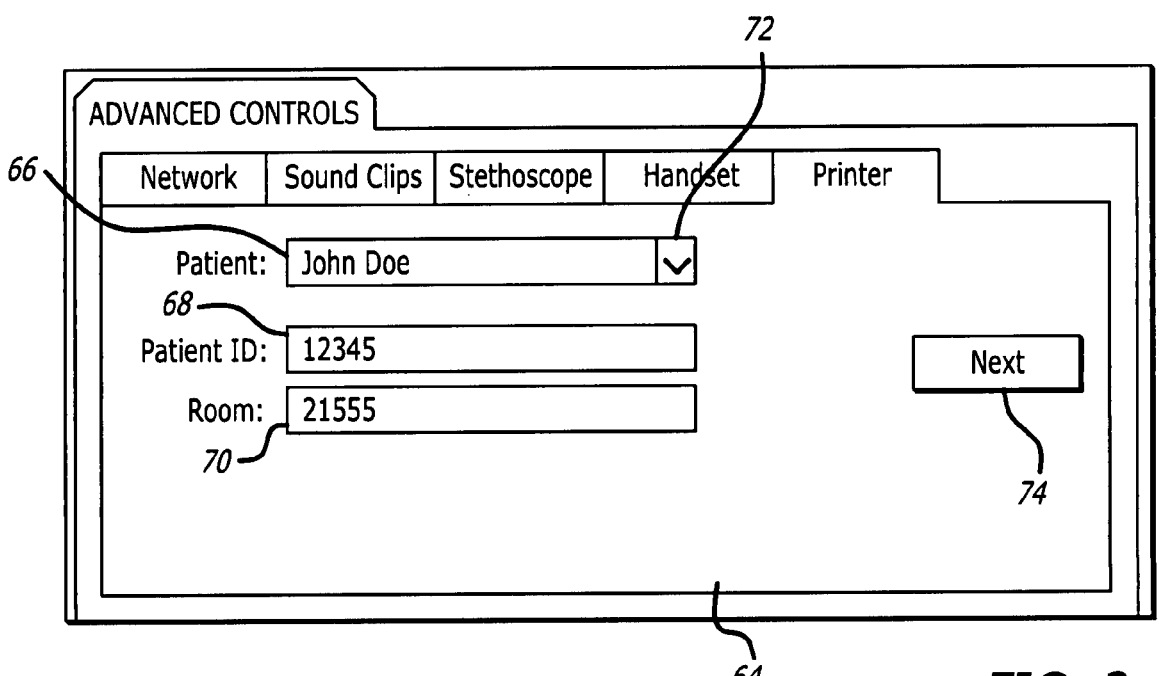
FIG. 3 is an illustration of a graphical user interface.

The remote control station 16 may display a plurality of graphical user interfaces. FIG. 2 shows a graphical user interface 60 that displays a plurality of tabs in an ADVANCED CONTROLS section of the station operating system. One of the tabs may be a PRINTER tab 62. Selection of the PRINTER tab 62 may cause the display of the graphical user interface 64 shown in FIG. 3. The interface 64 may include a PATIENT data field 66, a PATIENT ID data field 68 and a ROOM data field 70. The user can enter appropriate data into the fields 66, 68 and 70. The PATIENT field 66 may include a drop down button 72 that can be selected to display a drop down menu with the names of patients that have been stored and/or previously entered into the system. Selecting one of the names from the drop down menu can cause the automatic population of the PATIENT ID 68 and ROOM 70 fields, respectively.

Figure 4:
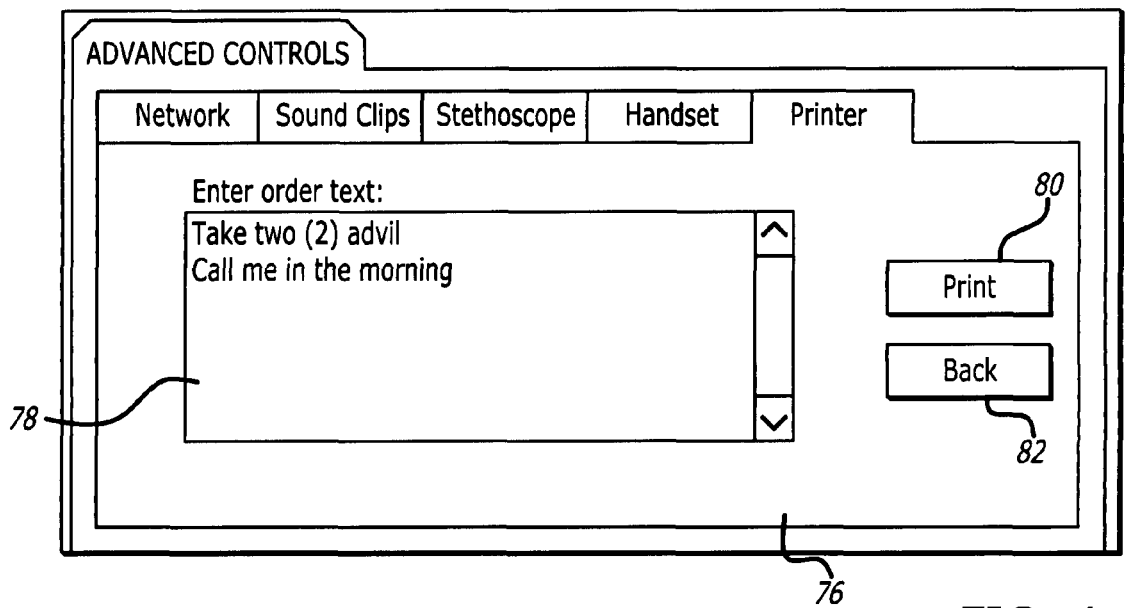
FIG. 4 is an illustration of a graphical user interface.

The user can select the NEXT button 74 which may cause the display of the graphical user interface 76 shown in FIG. 4. The graphical user interface 76 may have a ENTER ORDER TEXT data field 78. The field 78 allows a user to enter information such as a medical prescription. The user can then select a PRINT button 80 which causes the remote control station to send the information entered into fields 66, 68, 70 and/or 78 to the robot. The robot printer then prints the information in fields 66, 68, 70 and/or 78. The interface 76 may also have a BACK button 82 that can be selected to re-display the graphical user interface 64. The user can then repeat the process for a new prescription order and/or patient.

Figure 5:
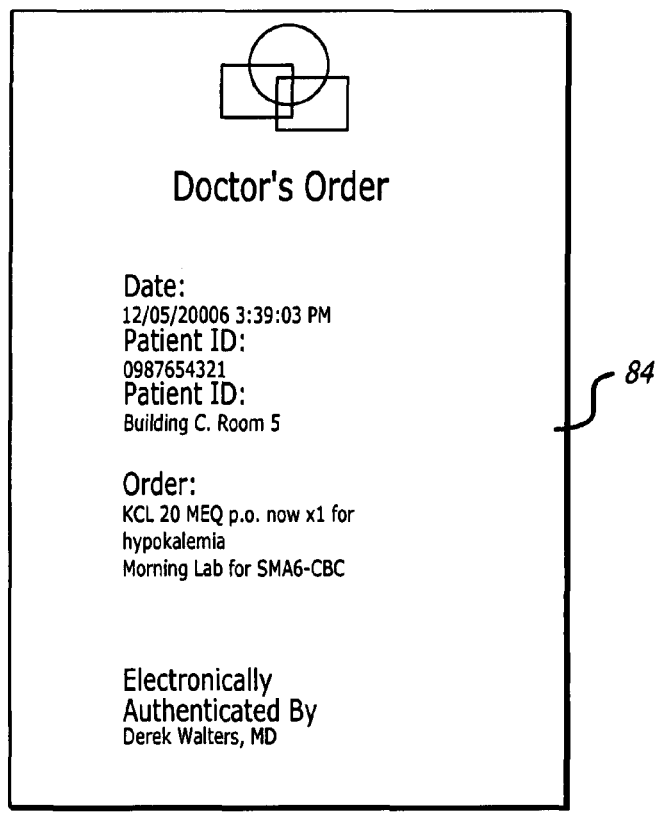
FIG. 5 is an illustration of a print-out.

FIG. 5 provides an example of a print-out 84 of the information provided by the remote station. The system allows a doctor to remotely observe and diagnose a patient, and provide a medical prescription through the robot and printer.

Figure 6:
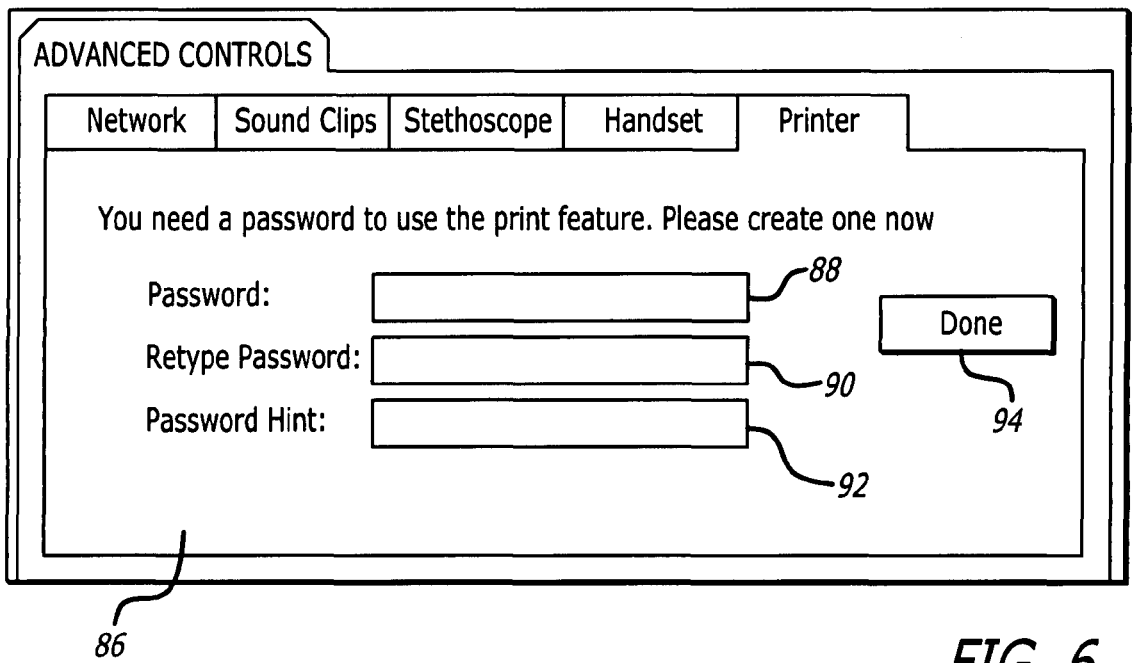
FIG. 6 is an illustration of a graphical user interface.

The system may allow for password authentication to print the information. It may be desirable to insure that the information is electronically authenticated to prevent unauthorized personnel from ordering prescriptions. FIG. 6 shows a graphical user interface 86 with a PASSWORD data field 88, a RETYPE PASSWORD data field 90 and a PASSWORD HINT data field 92. The user can create a password by entering relevant information into fields 88 and 90. A password hint can be entered into field 92. The creation of the password and hint can be completed by selecting the DONE button 94.

Figure 7:
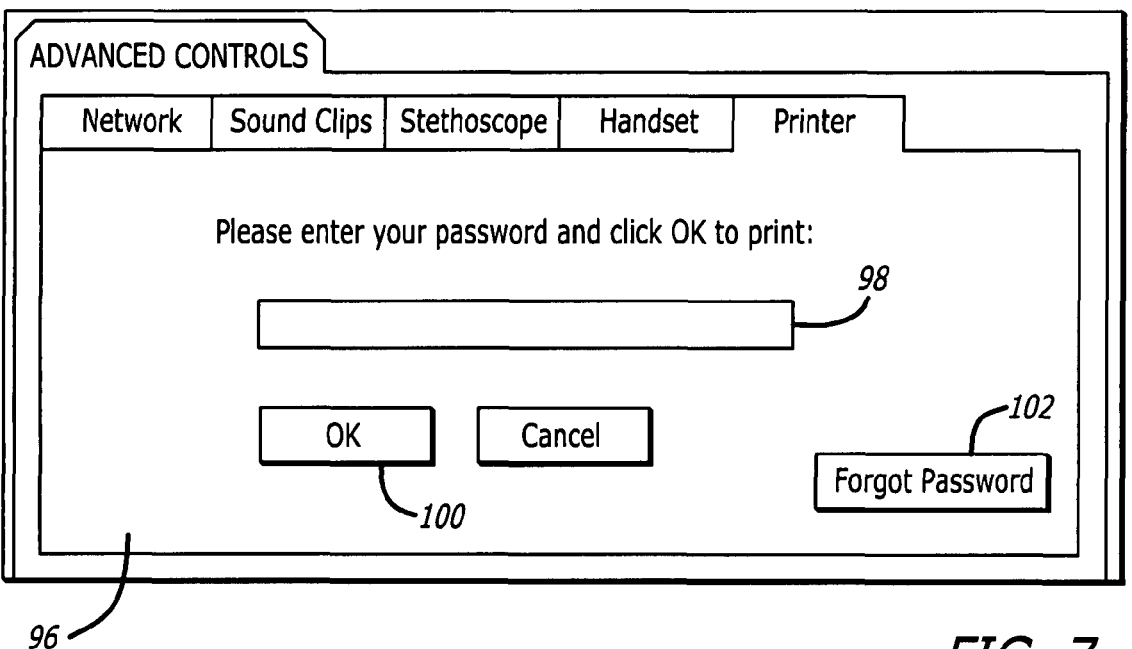
FIG. 7 is an illustration of a graphical user interface.

Selecting the PRINT button 78 in the graphical user interface 74 can cause the display of the graphical user interface 96 shown in FIG. 7. The interface 96 includes a PASSWORD data field 98 that allows the user to enter their password. The user can then select an OK button 100 to cause the information (e.g., data in fields 66, 68, 70 and/or 78) to be printed by the robot printer. If the entered password is incorrect a prompt may be displayed so the user enters a new password or selects the FORGOT PASSWORD button 102 to display the hint that was created in field 92 of interface 88.

Figure 8:
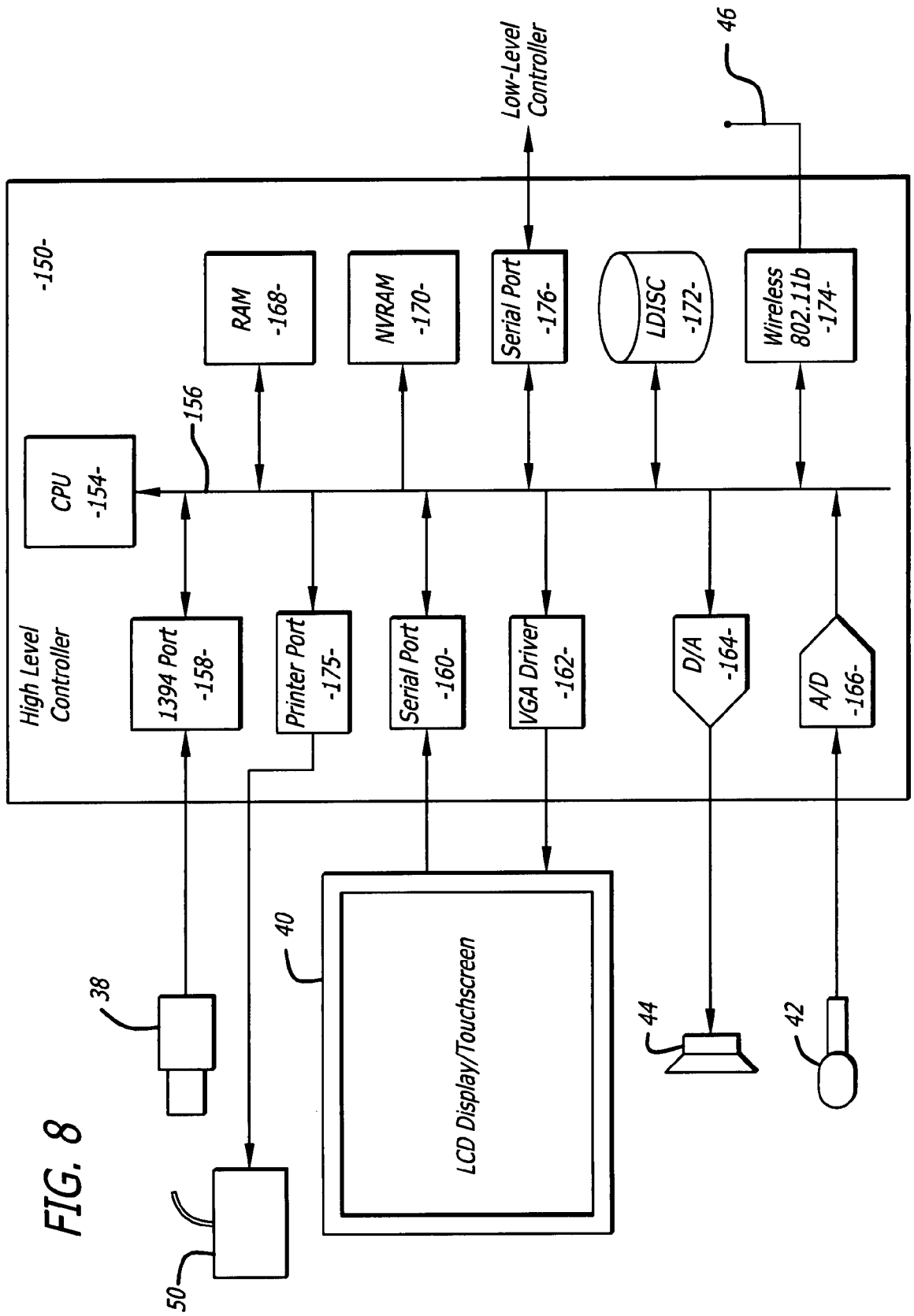
FIG. 8 is a schematic of an electrical system of the robot.
Figure 9:
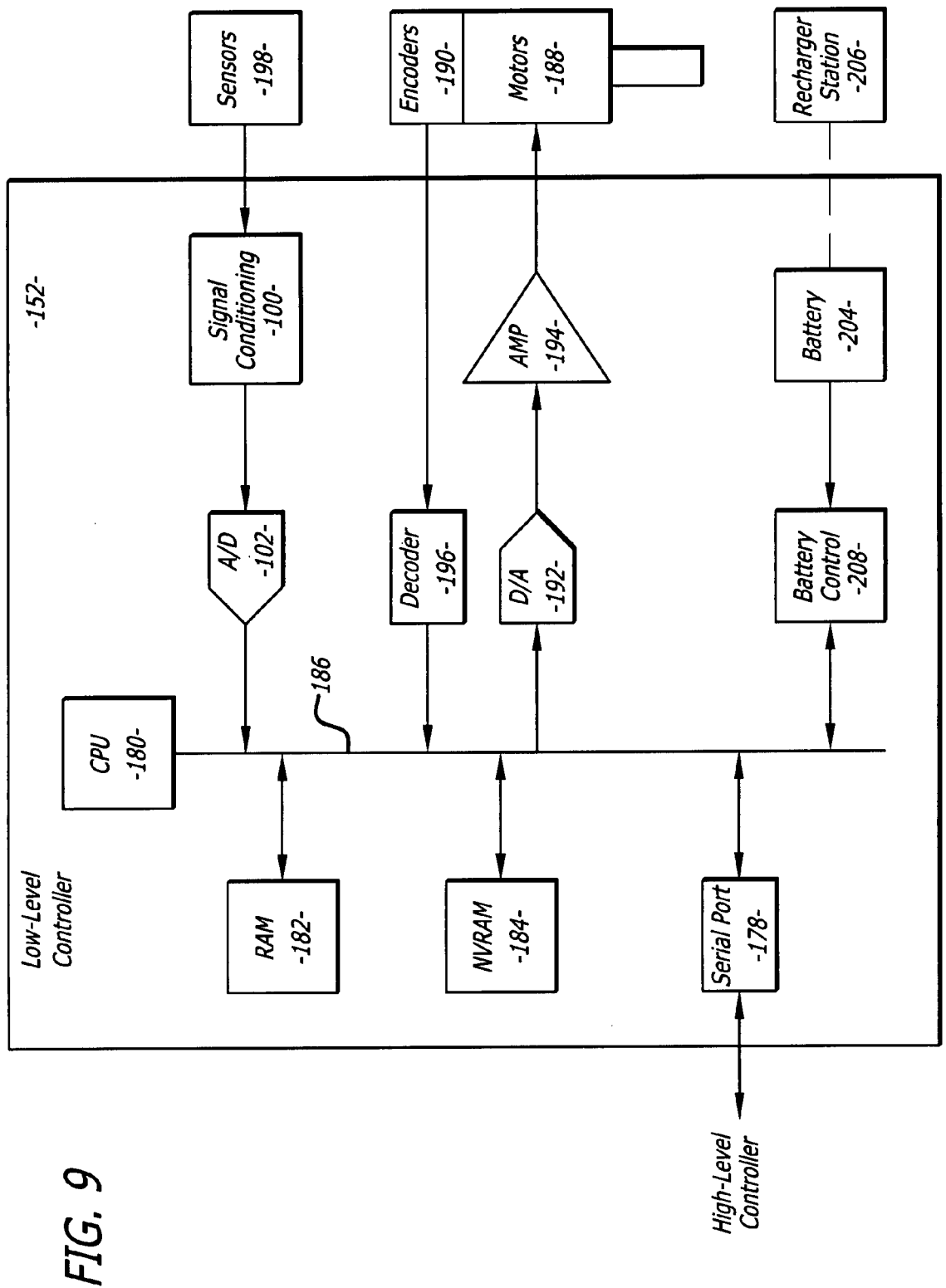
FIG. 9 is a further schematic of the electrical system of the robot.

FIGS. 8 and 9 show an embodiment of a robot 12. Each robot 12 may include a high level control system 150 and a low level control system 152. The high level control system 150 may include a processor 154 that is connected to a bus 156. The bus 156 is coupled to the camera 38 by an input/output (I/O) port 158. The monitor 40 is coupled to the bus 156 by a serial output port 160 and a VGA driver 162. The monitor 40 may include a touchscreen function that allows the patient to enter input by touching the monitor screen.

The speaker 44 is coupled to the bus 156 by a digital to analog converter 164. The microphone 42 is coupled to the bus 156 by an analog to digital converter 166. The high level controller 150 may also contain random access memory (RAM) device 168, a non-volatile RAM device 170 and a mass storage device 172 that are all coupled to the bus 156.

The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 174. By way of example, the transceiver 174 may transmit and receive information in accordance with IEEE 802.11b.

The printer 50 is coupled to the bus 156 by a serial output port 175. The serial port 175 may include a Universal Asynchronous Receiver/Transmitter ("UART") interface.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control communication between the robot 12 and the remote control station 16.

The remote control station 16 may include a computer that is similar to the high level controller 150. The computer would have a processor, memory, I/O, software, firmware, etc. for generating, transmitting, receiving and processing information.

The high level controller 150 may be linked to the low level controller 152 by serial ports 176 and 178. The low level controller 152 includes a processor 180 that is coupled to a RAM device 182 and non-volatile RAM device 184 by a bus 186. Each robot 12 contains a plurality of motors 188 and motor encoders 190. The motors 188 can actuate the movement platform and move other parts of the robot such as the monitor and camera. The encoders 190 provide feedback information regarding the output of the motors 188. The motors 188 can be coupled to the bus 186 by a digital to analog converter 192 and a driver amplifier 194. The encoders 190 can be coupled to the bus 186 by a decoder 196. Each robot 12 also has a number of proximity sensors 198 (see also FIG. 1). The sensors 198 can be coupled to the bus 186 by a signal conditioning circuit 200 and an analog to digital converter 202.

The low level controller 152 runs software routines that mechanically actuate the robot 12. For example, the low level controller 152 provides instructions to actuate the movement platform to move the robot 12. The low level controller 152 may receive movement instructions from the high level controller 150. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 204. The battery 204 may be recharged by a battery recharger station 206 (see also FIG. 1). The low level controller 152 may include a battery control circuit 208 that senses the power level of the battery 204. The low level controller 152 can sense when the power falls below a threshold and then send a message to the high level controller 150.

Figure 10:
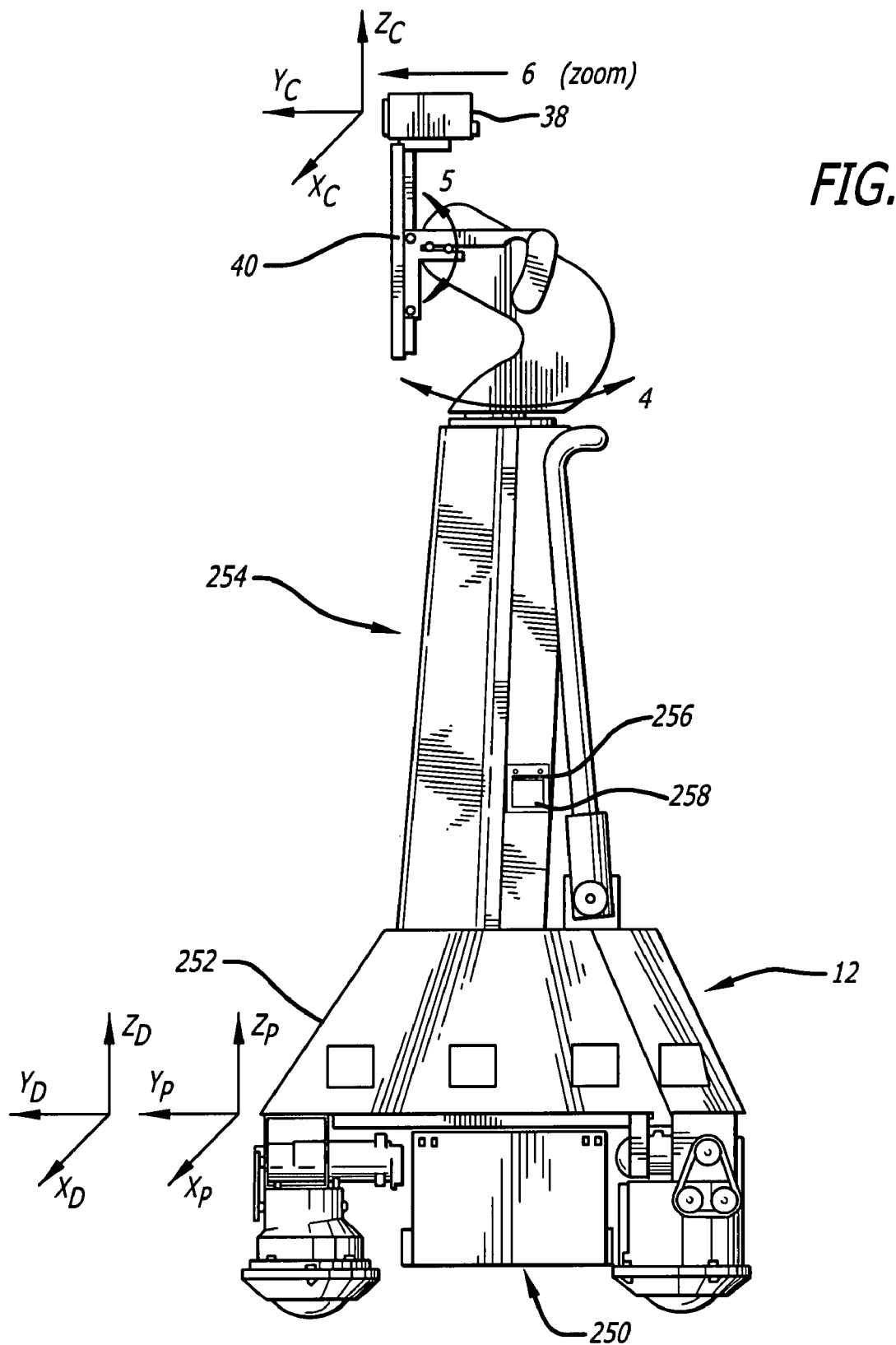
FIG. 10 is an illustration of a robot.

FIG. 10 shows an embodiment of the robot 12. The robot 12 may include a holonomic platform 250 that is attached to a robot housing 250. The holonomic platform 250 provides three degrees of freedom to allow the robot 12 to move in any direction.

The robot 12 may have a pedestal assembly 254 that supports the camera 38 and the monitor 40. The pedestal assembly 254 may have two degrees of freedom so that the camera 38 and monitor 40 can together be swiveled and pivoted as indicated by the arrows.

The platform 250 is located within a platform reference coordinate system that may have axes $X_p$, $Y_p$ and $Z_p$. By way of example, the y-axis $Y_p$ may extend from a nose of the platform 250. The camera 38 is fixed to a camera reference coordinate system that may have axes $X_c$, $Y_c$ and $Z_c$. The y-axis $Y_c$ may extend perpendicular from the camera lens. When the robot is initialized, the y-axis $Y_c$ of the camera coordinate system may be aligned with the y-axis $Y_p$ of the platform coordinate system. A forward pivoting of the joystick 32 (shown in FIG. 1) may cause a corresponding movement of the platform 250 in the direction of the y-axis $Y_p$ in the platform coordinate system.

The robot may have a drive vector that may have axes $X_d$, $Y_d$, and $Z_d$ that is mapped to the camera coordinate system, the platform coordinate system or some other system. By way of example, the y-axis $Y_p$ may extend in the direction of forward motion. Mapping includes the process of transforming an input command into a directional movement relative to one or more coordinate systems. The robot controller may perform certain algorithms to translate input commands to platform movement in accordance with a specified mapping scheme. For example, when the drive vector is mapped to the camera coordinate system the controller computes the drive vector of the input command relative to the camera coordinate system. In a platform mapping scheme the input drive vector is computed relative to the platform coordinate system. In yet another scheme the drive vector can be computed relative to another coordinate system, such as a world coordinate system (e.g. coordinate system relative to the ground) that is independent of the camera or platform coordinate systems. Mapping the drive vector to the camera coordinate system may be desirable because all movement would be relative to the image viewed by the user, providing a system that is intuitive to use.

A twisting of the joystick 32 may cause the camera 38 to swivel as indicated by arrows 4. For example, if the joystick 32 is twisted +45 degrees the camera 38 will pivot +45 degrees. Swiveling the camera 38 also moves the y-axis $Y_c$ of the camera coordinate system, because the y-axis $Y_c$ is fixed to the camera. This may be different than the drive direction. The remote station computer may operate a program to generate a command that will automatically rotate the platform 250 to realign the y-axis $Y_p$ of the platform coordinate system with the y-axis $Y_c$ of the camera coordinate system. For the above example, the platform 250 is rotated +45 degrees. This approach keeps the platform 250 aligned with the camera 38, so that any subsequent movement of the robot will be intuitive relative to the image provided by the camera. For example, a forward pivot of the joystick will induce a forward movement of the robot as viewed through the monitor of the remote station. In this driving scheme, the platform may not be aligned with the head. The computer may generate trajectory planning for the platform coordinate system to move into alignment with the head coordinate system over a period of time or distance traveled, with or without an initial delay in time or some distance.

The system may be configured so that pivotal movement of the joystick 32 may be mapped to a corresponding directional movement of the robot. For example, pivoting the joystick along a +45 degree may cause the robot to move in a +45 degree direction relative to the y-axis $Y_c$ of the camera coordinate frame. Alternatively, the camera may pan +45 degrees and the platform 250 may rotate +45 degrees before forward movement by the robot. The automatic panning and platform rotation causes the robot to move in a forward direction as depicted by the image provided by the camera. The robot may have a mode wherein the user can twist the joystick to pan the camera during robot movement such that the movement is not in the direction the camera is pointing. This allows the user to visually pan while moving the robot. The joystick may have a spring return that automatically returns the position of the stick when released by the user. This causes the camera to be aligned with the direction of movement.

In general the robot may have a number of different mapping schemes and relative, dependent or independent, movement between the camera, the platform and drive direction. Relative movement between the camera and platform may occur in a camera based mapping scheme, a platform based mapping scheme, or some other scheme.

Although, the automatic platform rotation commands have been described as be generated by the remote station computer, it is to be understood that the robot may determine the commands and signals necessary to re-orient the platform 250 and/or the camera 38. The robot 12 may include a potentiometer (not shown) that tracks the position of the camera and provides feedback to the low level controller 180. The low level controller 180 may automatically rotate the platform to align the y-axes $Y_c$ and $Y_p$ or otherwise compensate for camera movement. A mode button (not shown) may allow the operator to place the system in either a tracking mode or a normal mode. In the tracking mode the robot moves relative to the camera coordinate system so that movement is intuitive relative to the screen even when the camera is panned. In normal mode the robot moves within the platform coordinate system.

The robot 12 includes a printer 256 that prints information on printer paper 258. The information may be provided by a remote control station connected to the robot The system may be the same or similar to a robotic system provided by the assignee InTouch-Health, Inc. of Santa Barbara, Calif. under the name RP-7. The system may also be the same or similar to the system disclosed in U.S. Pat. No. 6,925,357 issued Aug. 2, 2005, which is hereby incorporated by reference.

Figure 11:
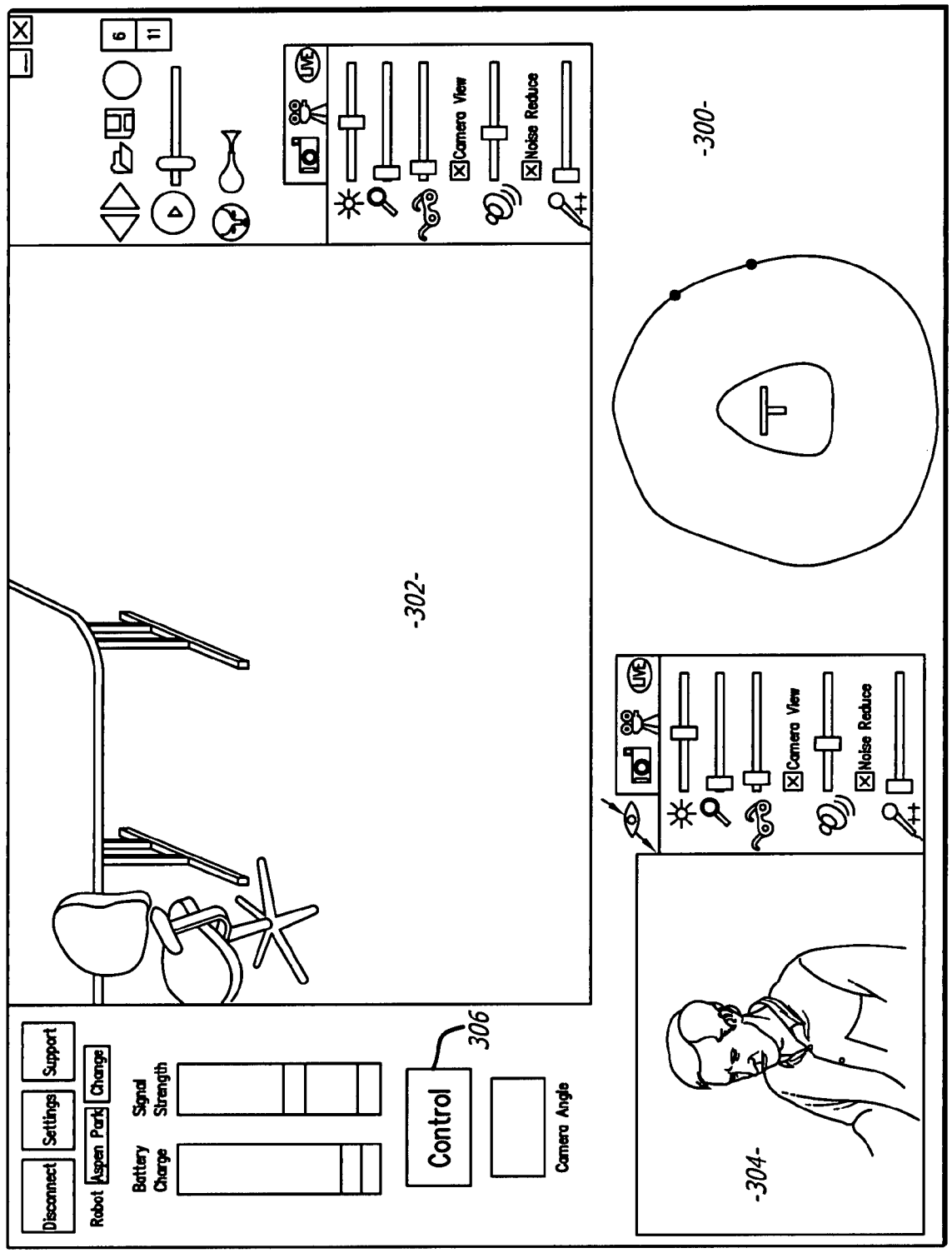
FIG. 11 is a graphical user interface of a remote station.

FIG. 11 shows a display user interface ("DUI") 300 that can be displayed at the remote station 16. The DUI 300 may include a robot view field 302 that displays a video image provided by the camera of the robot. The DUI 300 may also include a station view field 304 that displays a video image provided by the camera of the remote station 16. The DUI 300 may be part of an application program stored and operated by the computer 22 of the remote station 16. The display user interface and the various features and functions provided by the interface may be the same or similar as the DUI provided by the RP-7 system.

The DUI 300 may also have a control button 306 that can be selected to display the interface shown in FIG. 2.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control, the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The system 10 can be used for doctor proctoring where a doctor at the remote station provides instructions and feedback to a doctor located in the vicinity of the robot. For example, a doctor at the remote location can view a patient and assist a doctor at the patient location in a diagnosis. Likewise, the remote doctor can assist in the performance of a medical procedure at the robot location.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |

TABLE II-continued

| | Requesting User | | | | |
|---|---|---|---|---|---|
| | Local | Caregiver | Doctor | Family | Service |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |

TABLE III-continued

Control Commands

| Command | Example | Description |
| --- | --- | --- |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |
| print | print -doctor "<string>" -patient "<string>" -order "<string>" [-room "<string>"] [-id "<string>"] | The print command causes the robot printer to print accompanying information. |

Table IV provides a list of reporting commands that are generated by the robot and transmitted to the remote station through the network.

TABLE IV

Reporting Commands

| Command | Example | Description |
| --- | --- | --- |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |

TABLE IV-continued

Reporting Commands

| Command | Example | Description |
| --- | --- | --- |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 154 of the robot high level controller 150 may operate a program that determines whether the robot 12 has received a robot control command within a time interval. For example, if the robot 12 does not receive a control command within 2 seconds then the processor 154 provides instructions to the low level controller 150 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may also have internal safety failure features. For example, the robot may monitor communication between the robot controller and the robot servo used to operate the platform motors. The robot monitor may switch a relay to terminate power to the platform motors if the monitor detects a lack of communication between the robot controller and the motor servo.

The remote station may also have a safety feature for the input device 32. For example, if there is no input from the joystick for a certain time interval (e.g. 10 seconds) the computer 22 may not relay subsequent input unless the user presses a button for another time interval (e.g. 2 seconds), which reactivates the input device.

Figure 12:
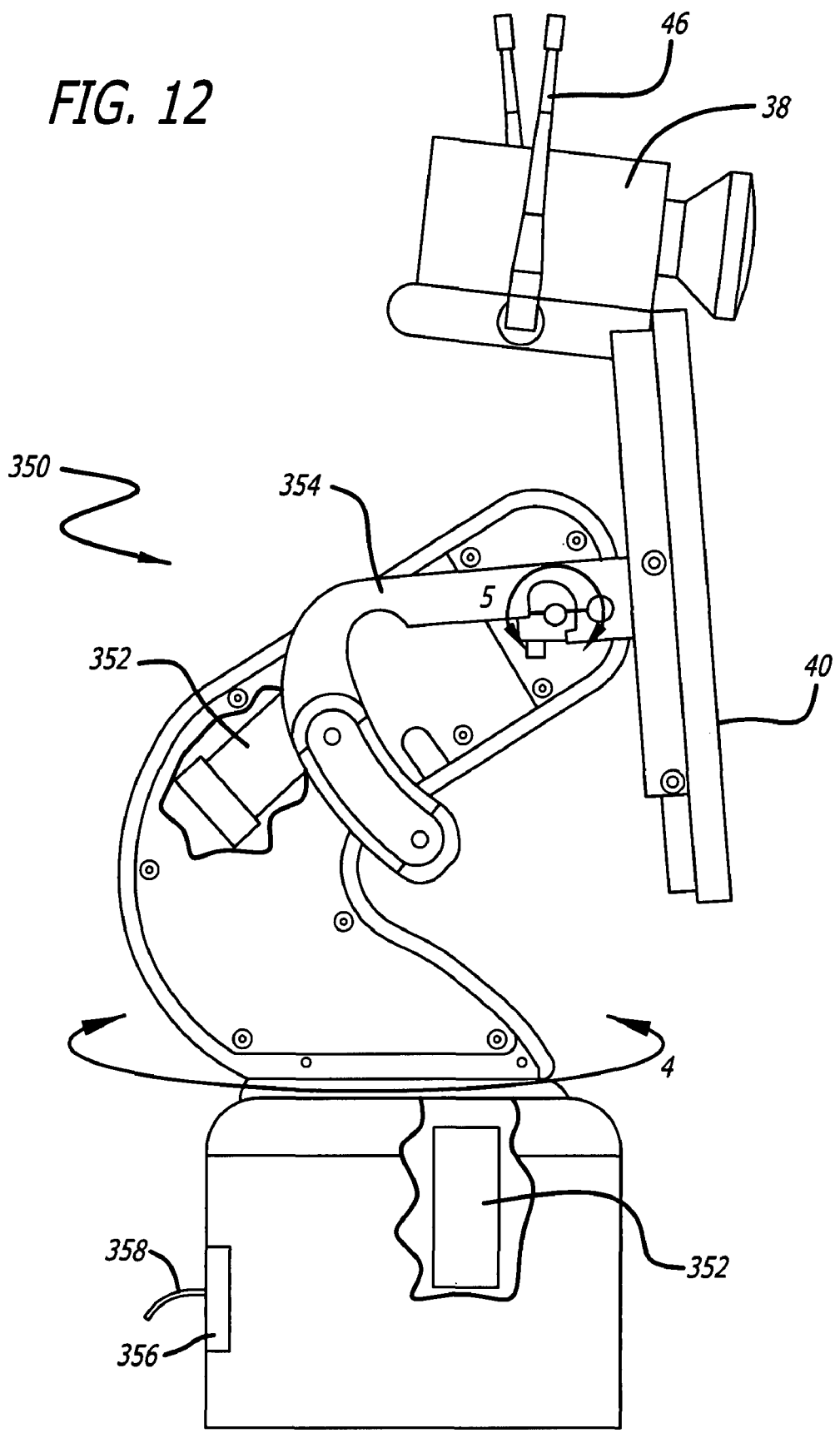
FIG. 12 is an illustration of a robot head.

FIG. 12 shows another embodiment of the robot as a robot head 350 that can both pivot and spin the camera 38 and the monitor 40. The robot head 350 is controlled by a user operating a control station. The robot head 350 can be similar to the robot 12 but without the platform 250. The robot head 350 may have actuators 352 and linkages 354 to pivot the camera 38 and monitor 40 about a pivot axis 4, and spin the camera 38 and monitor 40 about a spin axis 5. The pivot axis may intersect the spin axis. Having a robot head 350 that both pivots and spins provides a wide viewing area.

The robot head 350 may be in the system either with or instead of the mobile robot 12. The robot head can be particularly useful for doctor proctoring. The head can be located at a medical facility such as an emergency room or a doctor's office. A doctor at the remote location can assist in the diagnosis and medical treatment of a patient located at the robot location. The doctor can move the head to view the patient through control commands from the remote control station. Doctor proctoring can also be performed with a mobile robot 12.

The robot head 350 has a printer 356 that can print information on printer paper 358. The information may be provided by a remote control station connected to the robot head.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

Although a printer is shown and described, the robot may have other mechanisms, subassemblies, etc. that create a tangible object in response to commands and instructions from the remote station. For example, the robot may include a 3-D rapid prototyping output device. For example, the rapid prototyping device may be a product sold by Desktop Factory of Pasadena, Calif. The remote station may include 3-D modeling software. For example, the remote station may have an Autodesk 3-D modeling software. The user at the remote station can create a 3-D model and then transmit the data to the robot. The data can include a series of software instructions and data, collectively referred to as commands, that can be interpreted to build the model. The robot then processes the data to create a physical model with its rapid prototyping output device.

What is claimed is:

1. A remote controlled telepresence robot system, comprising:
    a robot that includes a mobile platform, a camera that captures a robot image, a monitor, a speaker and a microphone coupled to said mobile platform;
    a printer coupled to said robot; and,
    a remote control station that controls said robot and provides information to said robot that is printed by said printer, said remote control station including a monitor coupled to said robot camera to display said robot image, a camera that captures an operator image that is displayed by said robot monitor, a speaker coupled to said robot microphone and a microphone coupled to said robot speaker.

2. The system of claim 1, wherein said remote control station includes one or more graphical user interfaces with a plurality of data fields.

3. The system of claim 2, wherein one of said data field includes a user password.

4. The system of claim 2, wherein one of said data fields is a prescription order field.

5. The system of claim 2, wherein one of said data fields includes a patient field.

6. The system of claim 1, wherein said robot monitor and said camera move together in at least two degrees of freedom.

7. The system of claim 1, further comprising a medical prescription printed by said printer.

8. A method for remotely printing information with a remote controlled telepresence mobile robot, comprising:
    transmitting information from a remote control station to a mobile robot, the mobile robot including a mobile platform, and a camera that captures a robot image, a monitor, a speaker and a microphone coupled to the mobile platform, the remote station including a monitor coupled to the robot camera to display said robot image, a camera that captures an operator image that is displayed by the robot monitor, a speaker coupled to the robot microphone and a microphone coupled to the robot speaker; and,
    printing the information from a printer coupled to the mobile robot.

9. The method of claim 8, wherein the remote control station displays one or more graphical user interfaces with a plurality of data fields.

10. The method of claim 9, wherein a user enters a user password into one or more of the data fields.

11. The method of claim 9, wherein a user enters a prescription order into one or more of the data fields and the prescription order is printed by the robot printer.

12. The method of claim 9, wherein a user enters patient information into one or more of the data fields and the patient information is printed by the robot printer.

* * * * *